(12) United States Patent
Williamson et al.

(10) Patent No.: US 8,479,441 B2
(45) Date of Patent: Jul. 9, 2013

(54) LIGHT DISTRIBUTION APPARATUS FOR CULTIVATION OF PHYTOPLANKTON AND OTHER AUTOTROPHIC AQUATIC SPECIES IN AN AQUATIC MEDIUM

(75) Inventors: Glen Stafford Williamson, Peoria, AZ (US); Jason DiBari, Oakland, CA (US)

(73) Assignee: Source Integration, Inc., Cambridge, MA (US)

( * ) Notice: Subject to any disclaimer, the term of this patent is extended or adjusted under 35 U.S.C. 154(b) by 448 days.

(21) Appl. No.: 12/483,173

(22) Filed: Jun. 11, 2009

(65) Prior Publication Data
US 2009/0320362 A1    Dec. 31, 2009

Related U.S. Application Data

(60) Provisional application No. 61/131,515, filed on Jun. 11, 2008.

(51) Int. Cl.
*A01G 7/00* (2006.01)
(52) U.S. Cl.
USPC ............................................................ 47/1.4
(58) Field of Classification Search
USPC ............................................................. 47/1.4
See application file for complete search history.

(56) References Cited

U.S. PATENT DOCUMENTS

| | | | | |
|---|---|---|---|---|
| 3,928,142 A | * | 12/1975 | Smith | 435/284.1 |
| 3,955,317 A | * | 5/1976 | Gudin | 435/420 |
| 4,137,868 A | * | 2/1979 | Pryor | 119/212 |
| 4,217,728 A | * | 8/1980 | Shimamatsu et al. | 47/1.4 |
| 4,253,418 A | * | 3/1981 | Lockwood et al. | 119/236 |
| 4,267,038 A | * | 5/1981 | Thompson | 210/602 |
| 4,676,956 A | * | 6/1987 | Mori | 422/186 |
| 4,900,678 A | * | 2/1990 | Mori | 435/292.1 |
| 4,952,511 A | * | 8/1990 | Radmer | 435/292.1 |
| 5,162,051 A | * | 11/1992 | Hoeksema | 47/1.4 |
| 5,536,398 A | * | 7/1996 | Reinke | 210/167.22 |
| 6,037,170 A | * | 3/2000 | Sekine | 435/292.1 |
| 6,083,740 A | * | 7/2000 | Kodo et al. | 435/266 |
| 6,370,815 B1 | | 4/2002 | Skill et al. | |
| 7,618,813 B2 | * | 11/2009 | Lee et al. | 435/292.1 |
| 7,682,821 B2 | * | 3/2010 | Woods et al. | 435/292.1 |
| 2003/0059932 A1 | | 3/2003 | Craigie et al. | |
| 2006/0207168 A1 | * | 9/2006 | Harper | 47/1.4 |

(Continued)

FOREIGN PATENT DOCUMENTS

| | | | |
|---|---|---|---|
| DE | 3536349 A1 | * | 4/1987 |
| DE | 10312505 A1 | * | 9/2004 |

(Continued)

*Primary Examiner* — Son T Nguyen
(74) *Attorney, Agent, or Firm* — Brian Beverly; Beeson Skinner Beverly, LLP

(57) ABSTRACT

An apparatus for cultivation of phytoplankton and other autotrophic aquatic species in an aquatic medium in one embodiment comprises a plurality of liquid-impermeable transparent baffles, each forming an elongated trough-like enclosure, depending from a transparent top chamber, each baffle in communication with the top chamber, and two end walls for enclosing the top chamber and baffles. Introduction of water into the baffles sinks the apparatus in the liquid medium to the top of the baffles, leaving the top chamber above the surface of the medium. Light to which the top panel is exposed passes through the top chamber, the water in the baffles, and the baffles to encourage growth of selected microscopic organisms in the surrounding medium.

8 Claims, 11 Drawing Sheets

U.S. PATENT DOCUMENTS

| | | | |
|---|---|---|---|
| 2007/0155006 A1* | 7/2007 | Levin | 435/292.1 |
| 2007/0289206 A1* | 12/2007 | Kertz | 47/1.4 |
| 2008/0160591 A1 | 7/2008 | Willson et al. | |
| 2009/0011492 A1 | 1/2009 | Berzin | |
| 2009/0023199 A1 | 1/2009 | Gal | |

FOREIGN PATENT DOCUMENTS

| | | |
|---|---|---|
| EP | 0239272 | 9/1987 |
| JP | 2003057157 A * | 2/2003 |
| WO | 2010/144868 | 12/2010 |

* cited by examiner

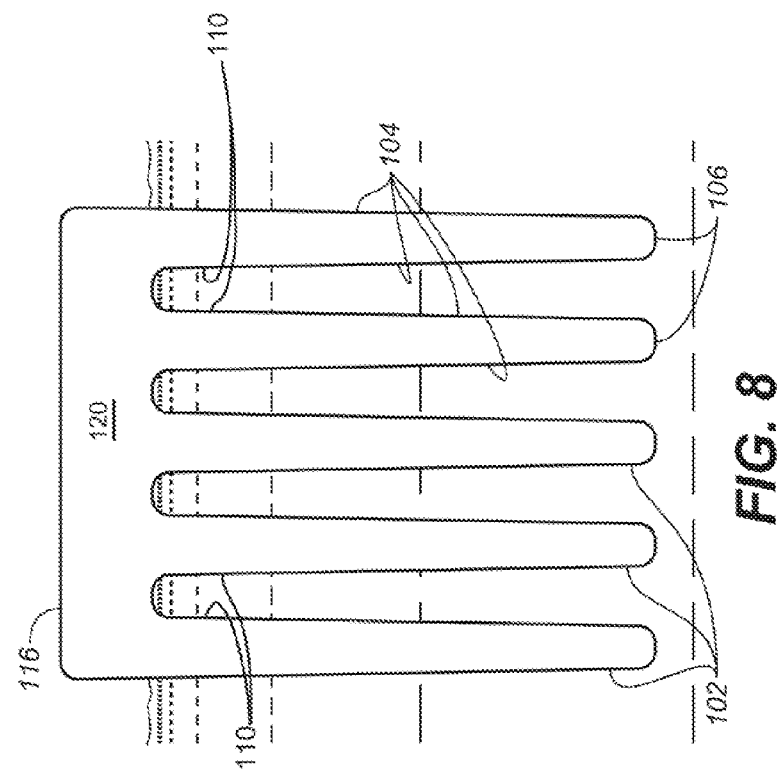
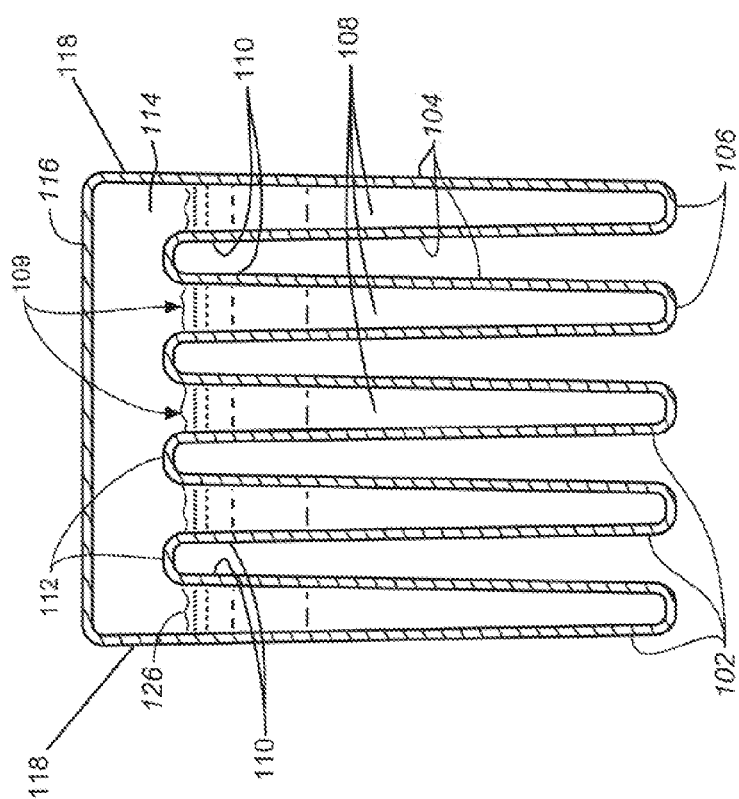
FIG. 7
FIG. 8

US 8,479,441 B2

LIGHT DISTRIBUTION APPARATUS FOR CULTIVATION OF PHYTOPLANKTON AND OTHER AUTOTROPHIC AQUATIC SPECIES IN AN AQUATIC MEDIUM

BACKGROUND OF THE INVENTION

Hundreds of species of phytoplankton, algae, autotrophic bacteria, and other autotrophic species occur naturally in both fresh water and oceans throughout the world. Long known as a potential diet supplement, and for certain species a dietary staple for nutritional needs, algae are now being cultivated for diverse purposes including the production of food for fish, mollusks, animals and humans, the treatment of sewage and waste waters and as nutriceutical ingredients and for the production of enzymes having industrial uses. Genetic modification of algae is also now being done experimentally to yield cultures capable of extremely rapid growth and by this replication of custom materials reproduction.

Traditional means of cultivating algae and similar autotrophic aquatic species has been in shallow ponds or raceways, both indoors and outdoors, covered and uncovered. Coverings provide a means of limiting exposure to strong lighting sources as well as preventing random contamination by competing species. In most cases, however, since the cells of these unicellular or conjoined but undifferentiated cells need to be exposed to photonic energy directly, the limitation of the penetration of light rays to a few centimeters from the normal surface of the liquid has limited the usefulness of water more than a few centimeters in depth.

Yuan-Kun Lee, in his article "Enclosed Bioreactors for the Mass Cultivation of Photosynthetic Microorganisms: The Future Trend," TIBTECH, July 1986, p. 186-189 reviews a variety of recent mechanisms and designs of apparatus intended to provide light to a larger area than merely that of the surface of the liquid. Much attention has been devoted to attempts to distribute light energy evenly across the interface to the liquid medium which results in expensive schemes of custom lighting instruments or fiber optics and other high capital cost items. The present invention is a low cost means of allowing light penetration to almost any arbitrary depth below the surface. No specific means of regulating the uniformity of the distribution of photonic energy to the photosynthetic species is contemplated except that natural solar radiation is expected to be the primary source of light, supplemented only if and when necessary by artificially generated illumination.

SUMMARY OF THE INVENTION

In accordance with the present invention, a novel apparatus for the cultivation of phytoplankton and other autotrophic aquatic species, which can also be considered to be a photobioreactor, comprises:

1. A watertight container consisting in a preferred embodiment of a chamber composed of 5 sides constituting a rectangular shape tank, the 6th side being optionally covered by a transparent, or semi-transparent lid the degree of transparency of which may be varied to suit the species under cultivation.
2. One or more watertight, hollow enclosures having an opening at an uppermost surface and consisting of transparent materials, the degree of transparency of which may be varied to suit the species under cultivation and the means and type of light available.
3. A set of alignment guides fixed to a frame or to the walls of the container into which the hollow enclosure is interposed.
4. A latching mechanism by which the hollow enclosure is held below the level at which it would otherwise come to neutral buoyancy.
5. A frame which orients the hollow enclosure with respect to the surface of the liquid into which it is partially immersed, or similar features of placement and alignment as may be fixed to the interior walls of the tank.
6. A mechanism by which the hollow enclosure may be raised above the level at which it would otherwise come to neutral buoyancy to a height which allows the hollow enclosure to be entirely above the surface of the growth medium liquid.
7. A mechanism which provides one or more instances of a contact arm squeegee which can be applied to the external surfaces of the hollow enclosure when raised out of the growth medium liquid.
8. A drainage trough (or more than one) oriented below the squeegee contact arm which by virtue of a sloping orientation carries away by gravity the biomass material being removed from the surface of the hollow enclosure by the squeegee as it is drawn across the surface of the hollow enclosure.

BRIEF DESCRIPTION OF THE DRAWINGS

FIG. 7 is cross-sectional view of the light distribution apparatus shown in FIG. 6 taken along line 7-7.

FIG. 8 is an elevational end view of the light distribution apparatus shown in FIGS. 5-7 with the baffles immersed in a liquid medium up to the top chamber.

DETAILED DESCRIPTION OF THE ILLUSTRATED EMBODIMENTS

Figure 1:
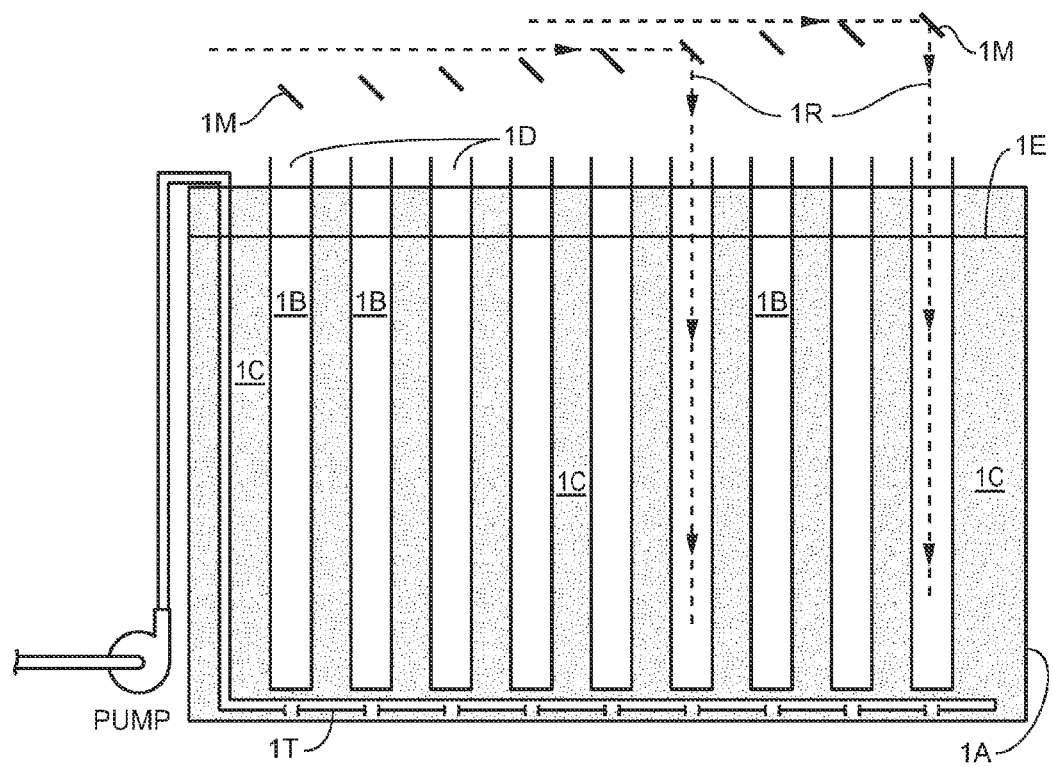
FIG. 1 is an elevational view of an apparatus for cultivation of phytoplankton and other autotrophic aquatic species in an aquatic medium according to the invention.

An apparatus for the cultivation of phytoplankton and other autotrophic aquatic species which may be used as a bioreactor for biomass production has:

(i) a substantially transparent chamber or tank (FIG. 1, #1A), the chamber being suitable for containing biomass in a liquid phase, and having a bottom and a number of sidewalls, the sidewalls being, in a preferred embodiment, a rectangular shape; although degree of transparency and rectangular shape are optional;

(ii) having one of more baffles (FIG. 1, #1B) consisting of transparent material which are inserted into the liquid growth medium (FIG. 1, #1C) from above, said baffle or baffles being of a liquid-impervious, hollow construction and open to the air on the uppermost surface (FIG. 1, #1D), said baffles in a preferred embodiment being of a rectangular shape in conformity to the chamber into which they are inserted, and dimensions proportional to those of the larger chamber such that the height of the baffle exceeds the level of the liquid (FIG. 1, #1E) in the chamber, and that the buoyancy of the hollow, watertight construction be counteracted by restraining clamps, or latches or similar holding mechanism (FIG. 2, #2L), and restrained from lateral displacement by guides (FIG. 2, #2G) affixed to the interior surface of the chamber, such guide mechanism being configured as two pairs of vertically aligned wheels on axles fixed (FIG. 2, #2A) to the sides of the chamber at each end of the baffle;

(iii) a circulating means for addition of and circulation of nutrients in the liquid phase, and by which nutrient gases and liquids (FIG. 1, #1T) may be added, by which circulation ensuring continual mixing of all of the nutrients with the growing species;

(iv) a means of reflective surface(s) (FIG. 1, #1M) by which natural or artificial light rays (FIG. 1, #1R) may be directed into the hollow baffles such that said light may penetrate into the liquid growth medium, not only at the liquid surface at the top of the chamber, (or in the case of transparent chamber through the transparent sides) but also through the transparent surfaces of the baffles on both sides and thus providing a semi-continuous exposure to a light source of the biomass in proximity to those baffle surfaces, and (v) a pump (FIG. 1, PUMP) by which nutrient gases and liquids are added to the growth medium.

An alternative embodiment could be deployed in bays, inlets or open ocean, or other naturally occurring bodies of water without a rigid tank portion, in which the orientation of the opening at the top of the hollow enclosures is controlled by gimbals tilting the entire baffle(s) and automated to track the angle of the Sun, thus the entire hollow baffles tilt and swivel (fully or partially) to track the path of the sun across the sky, such tilt being limited, of course, so as not to admit water into the hollow enclosures. Similarly another alternative embodiment is possible using gimbaled mirrored surfaces as solar collectors, with or without parabolic concentration reflectors by which natural or artificial light is directed into the hollow baffles (as in iv above).

FIG. 1 shows a plurality of instances of hollow enclosures in positions below that of buoyancy equilibrium in a transparent rectangular container filled with liquid and photosynthetic organisms.

Figure 2:
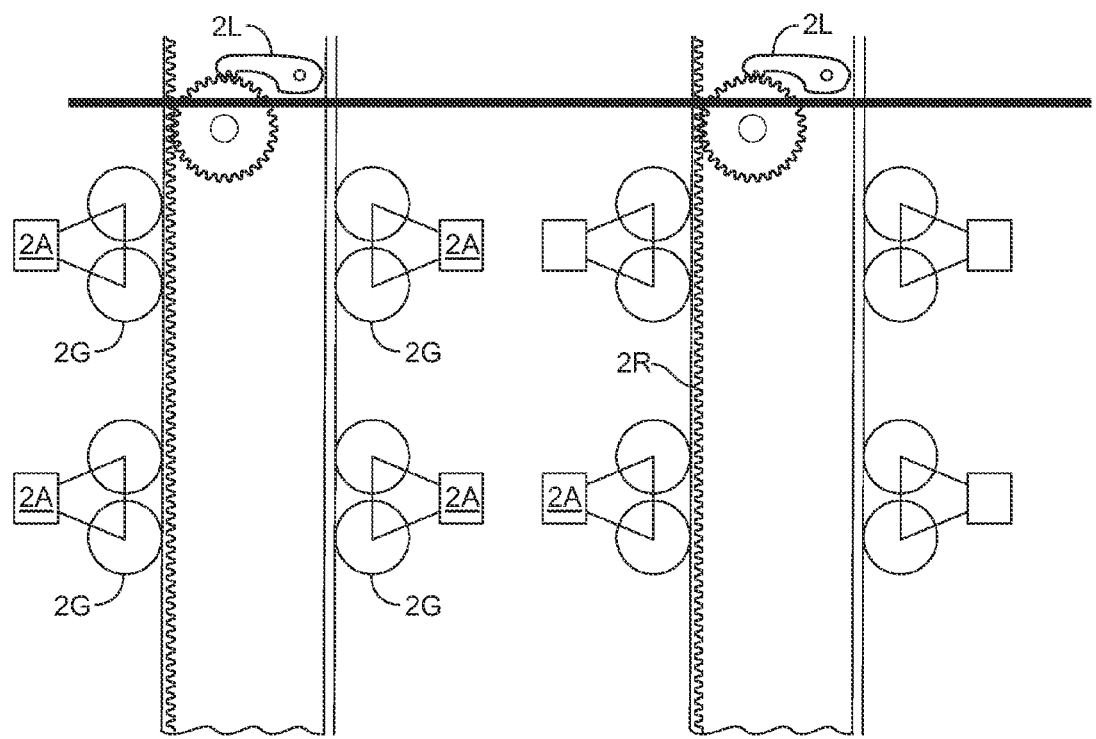
FIG. 2 is a detailed cross-sectional view of the uppermost portions of two enclosures of the apparatus shown in FIG. 1.

FIG. 2 shows the uppermost portions of two instances of the hollow enclosure in lateral cross section, held in vertical alignment by a set of alignment guides consisting of two sets of vertically aligned wheels on axles fixed at attachment points to the wall of the transparent rectangular container, while the hollow enclosure is being held below the position of neutral buoyancy by a latching mechanism (a palled rack and pinion, in the instances shown) the rack being fixed to the side of the hollow enclosure, while the pinion and pall are attached to the side of the tank.

Figure 3:
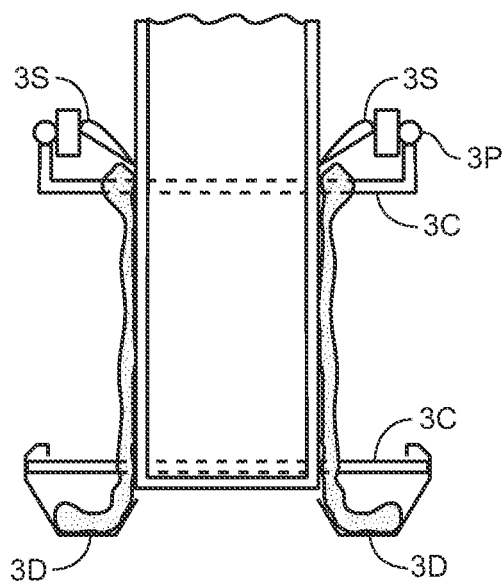
FIG. 3 is detailed elevational view of a squeegee contact arm and drainage trough used for harvesting organisms grow by the apparatus shown in FIG. 1.

FIG. 3 shows the approximate configuration of the squeegee contact arm (FIG. 3, #3S) and drainage trough (FIG. 3, #3D), illustrated as oriented as if at the bottom of the hollow enclosure when it is raised completely above the level of the growth medium liquid. Organisms being harvested are indicated by the gray zone on the surface of the baffles, and in the drainage trough. Contact arm contains spring-loaded hinges (FIG. 3, #3P) to hold squeegee at correct angles and both drainage troughs and contact arms have supporting cross-members (FIG. 3, #3C) joining the pairs on either side of the baffle when in use.

Figure 4:
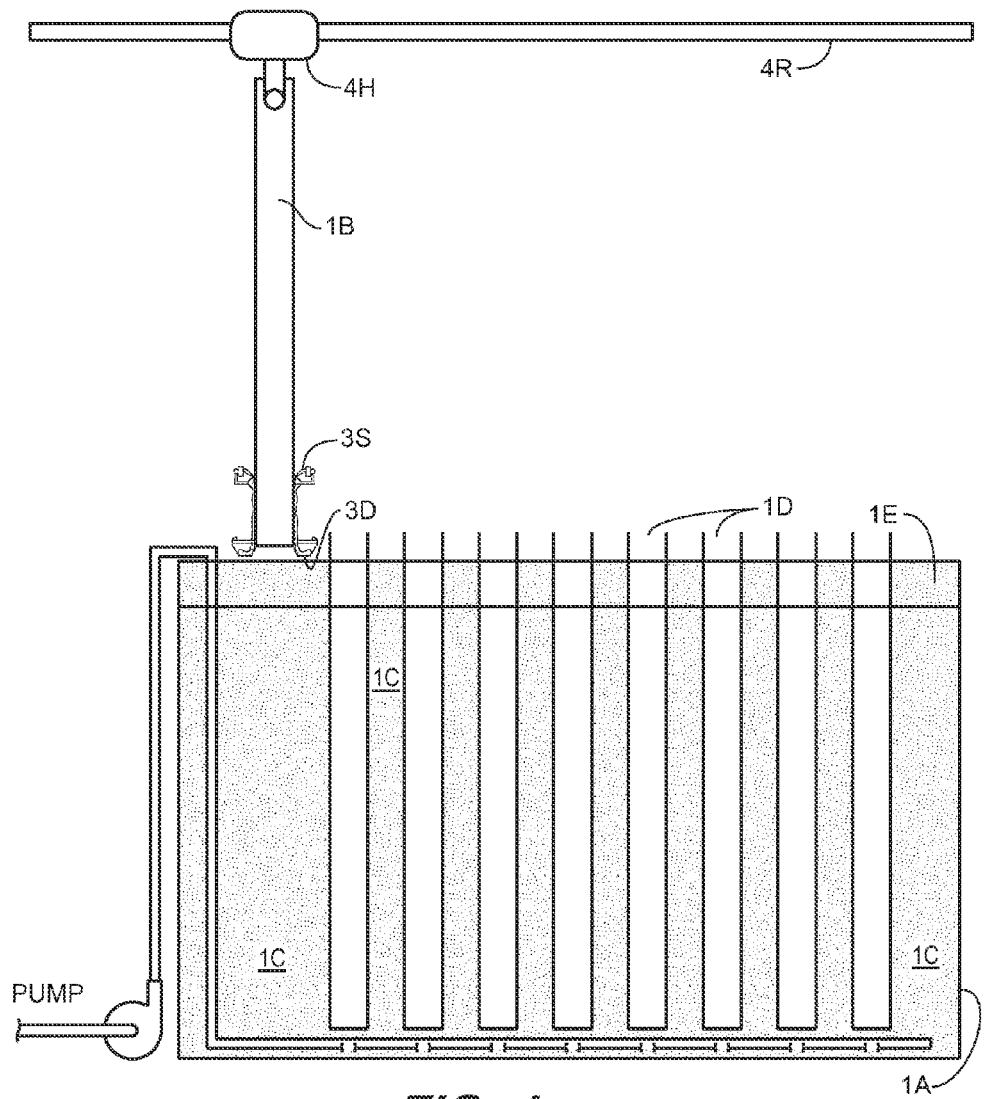
FIG. 4 is an elevational view of the apparatus depicted in FIG. 1 showing one enclosure elevated by a hoist mechanism above growth medium in a tank.
Figure 5:
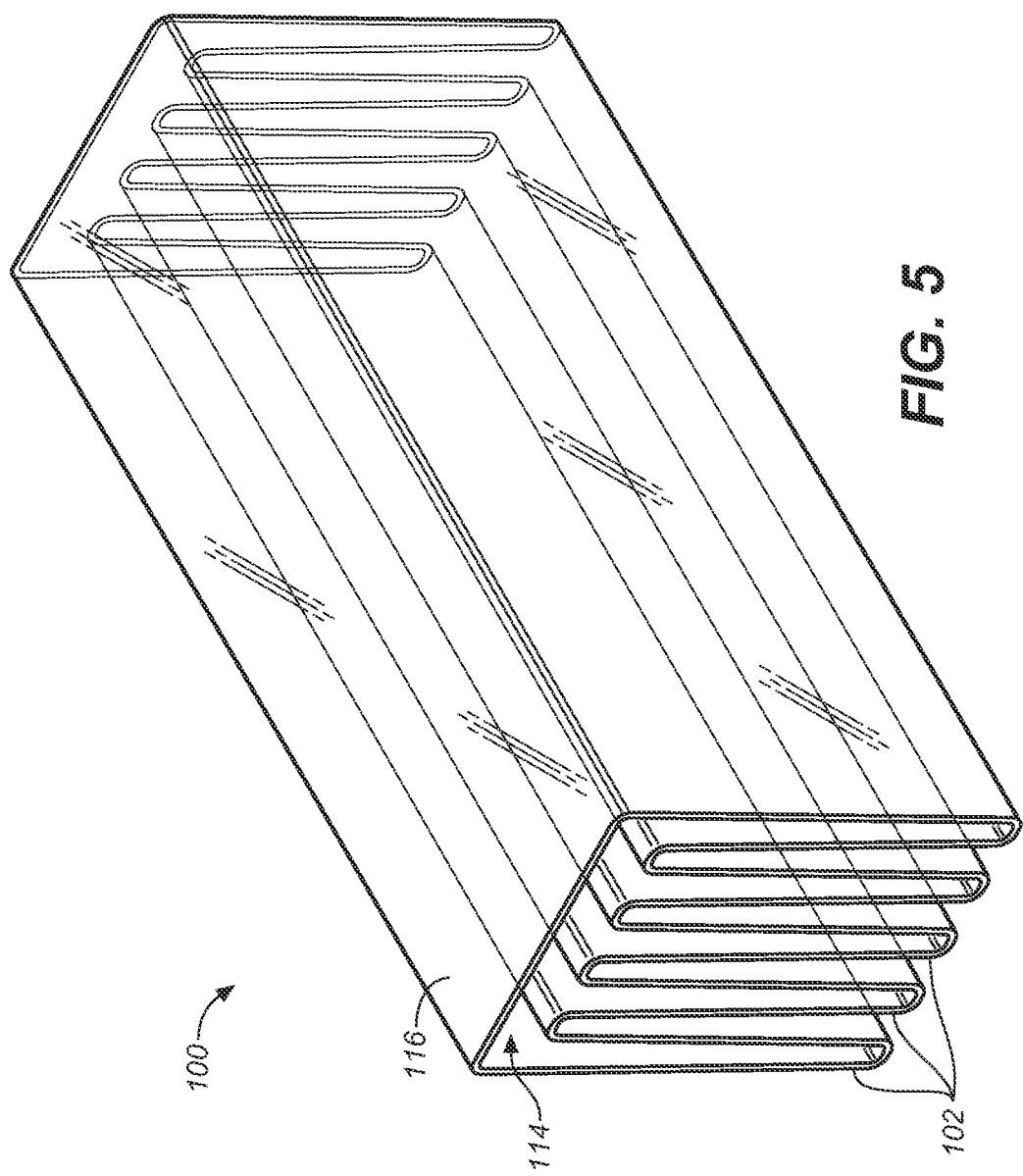
FIG. 5 is an upper perspective view of a light distribution apparatus for cultivation of phytoplankton and other autotrophic aquatic species in an aquatic medium according to the invention.
Figure 6:
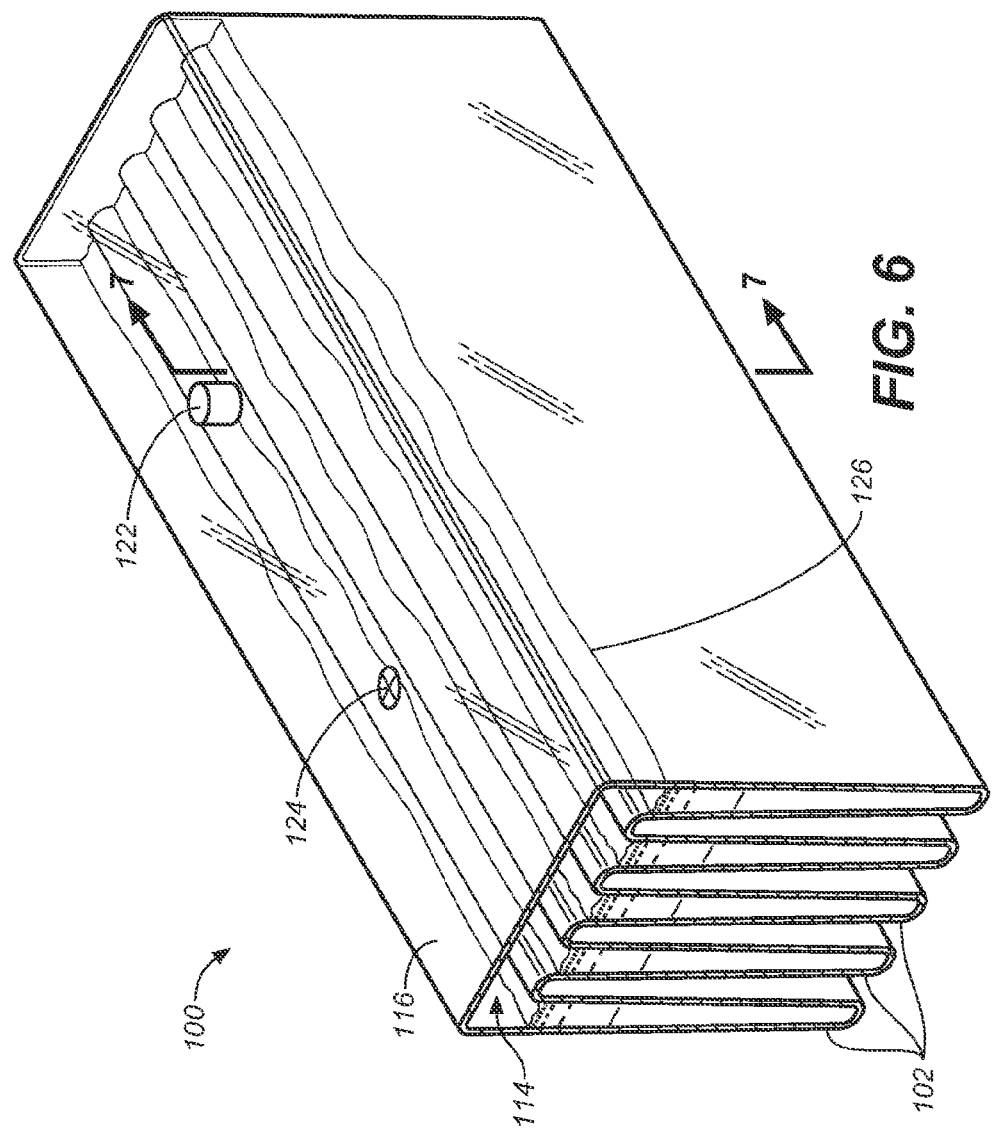
FIG. 6 is another upper perspective view of a light distribution apparatus similar to FIG. 5 but showing the baffles of the apparatus filled with water.
Figure 9:
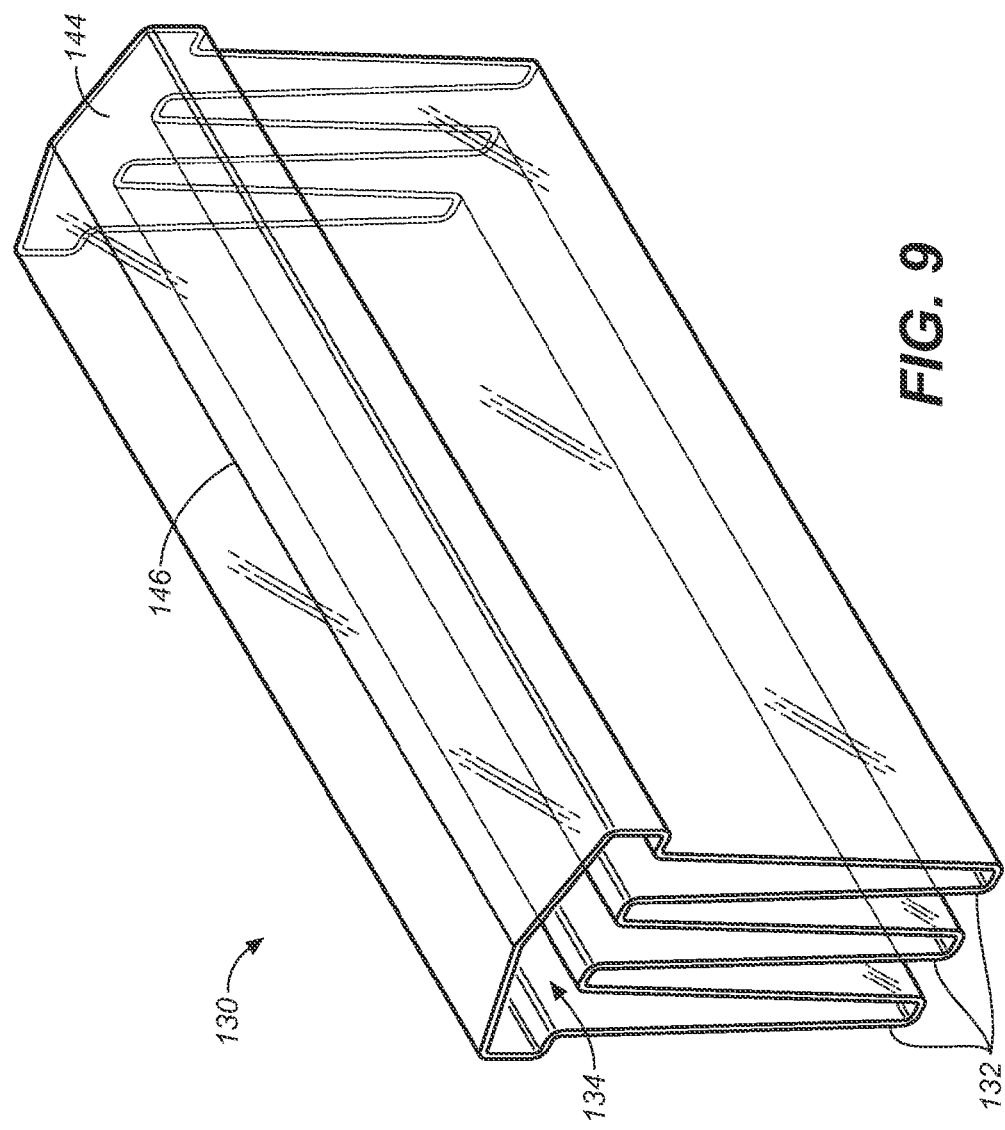
FIG. 9 is upper perspective view of another embodiment of a light distribution apparatus for cultivation of phytoplankton and other autotrophic aquatic species in an aquatic medium according to the invention.
Figure 10:
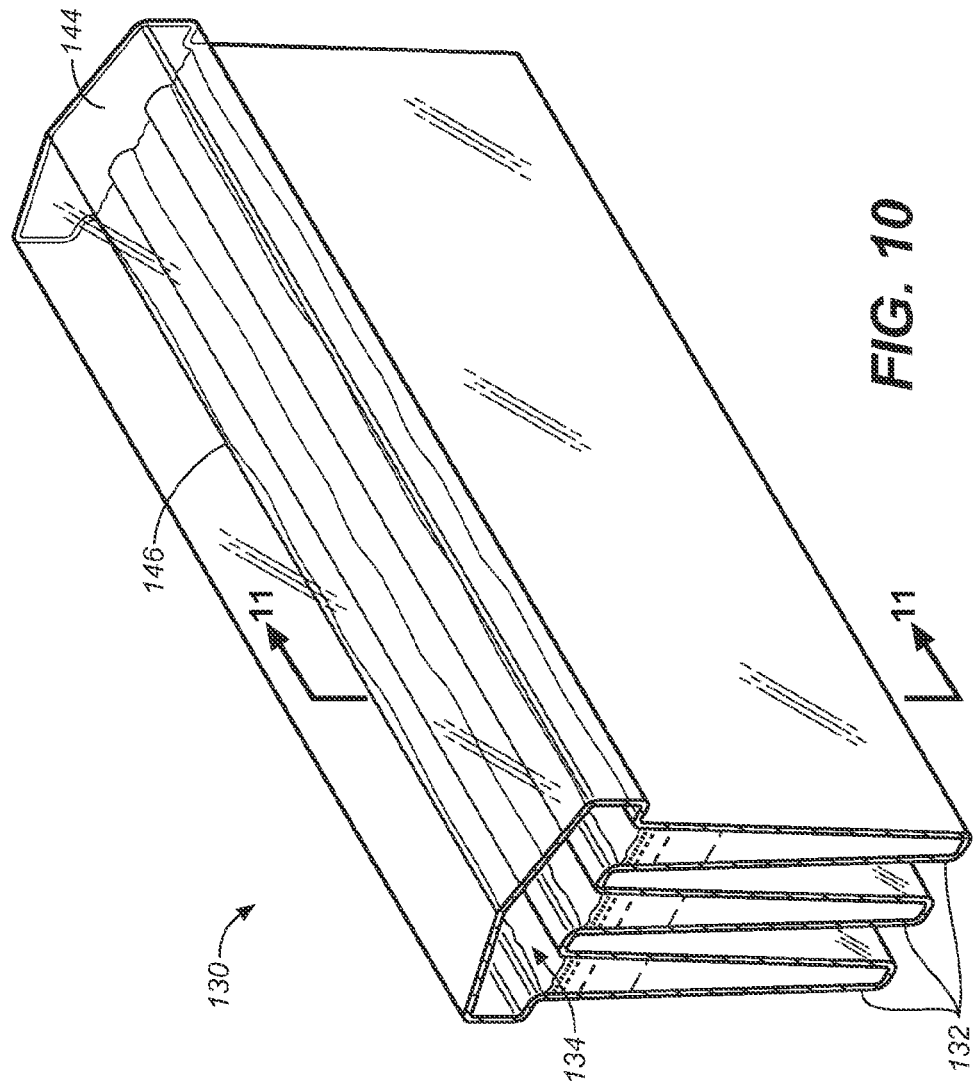
FIG. 10 is another upper perspective view of a light distribution apparatus similar to FIG. 9 but showing the baffles of the apparatus filled with water.
Figure 12:
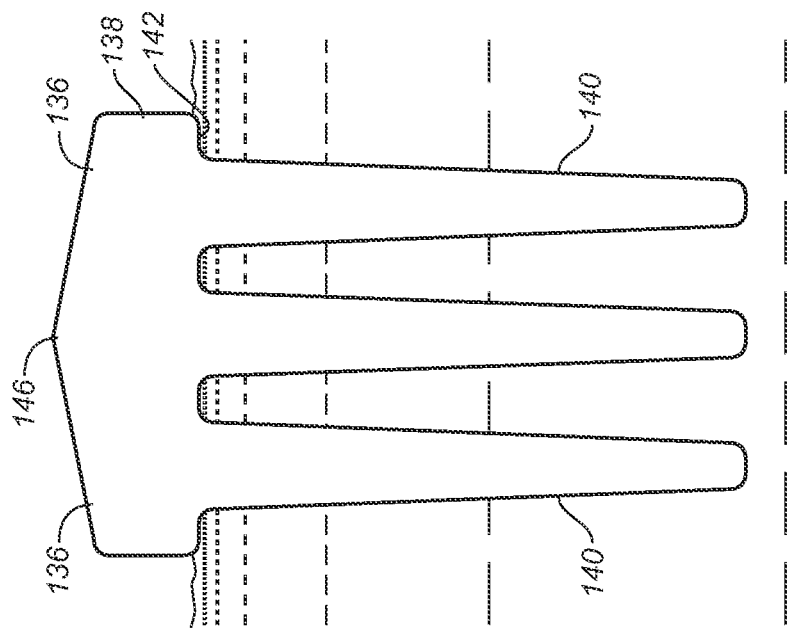
FIG. 12 is an elevational end view of the light distribution apparatus shown in FIGS. 9-11 with the baffles immersed in a liquid medium up to the top chamber.
Figure 11:
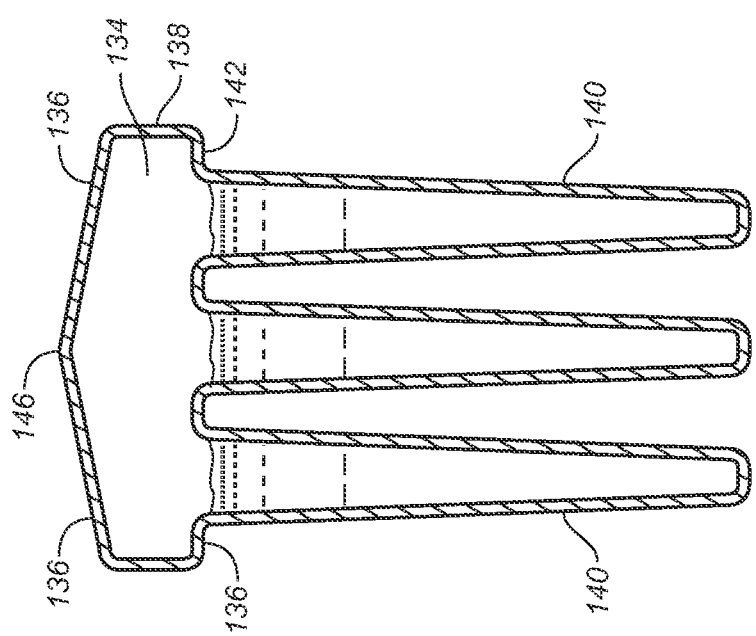
FIG. 11 is cross-sectional view of the light distribution apparatus shown in FIG. 10 taken along line 11-11.

FIG. 4 shows eight instances of the hollow enclosure in positions below that of buoyancy equilibrium in a transparent rectangular container filled with liquid and photosynthetic organisms therein, with the 9th instance thereof (FIG. 4, #1B) raised completely above the level of the growth medium liquid by a hoisting mechanism (FIG. 4, #4H), said hoisting mechanism attached to an overhead traveler rail (FIG. 4, #4R) suspended above the tank.

In one embodiment, the apparatus could be placed in either an interior or exterior environment, assuming sufficient heating or any needed cooling mechanical support was also supplied, natural light arriving at the tank indoors by means of mirrors and/or mylar interior reflective light tubes, supplemented during inclement weather or inhospitable seasonal sunlight by artificial lighting units. Transparency of the tank is optional, and would be governed by the photosensitivity of the specific species. Both freshwater and salt water varieties of phytoplankton, algae and other species can be raised in this apparatus, varying the supplements of carbon dioxide, nitrogen and other nutrients according to the needs of the particular species being cultivated. Some algae are grown for the nutriceuticals market, others for biomass, and still others specifically for their high lipid (oil) content for biofuels, but in every case contamination for other species and cross-contamination are a danger. The baffles, when raised above the growth liquid medium provide an easy means (via the squeegee scraping and drainage/harvesting troughs) to harvest from this apparatus. The hoist mechanism could, as described in the discussion of the drawings be on a traveler beam above all the tanks in a large production facility, or could be attached to a mobile cart moving from baffle to baffle in a single tank and from tank to tank to perform daily or weekly harvesting, depending on whether daily batching of partial harvests or phased series of harvests of only mature crops are desired.

One of the principal benefits of this apparatus is that it provides a much larger "surface" exposed to light than merely the normal surface of a body of liquid. As anyone who has walked along almost any rocky coast at low tide knows, algae grow not only at the surface level as they attach themselves to the rocks, they, fairly typically, tend to grow in all regions which receive some moderate amount of sunlight (multiple times) each day as the tide goes out and returns hours later. Although raising and removing the baffles and then very slowly allowing them to descend into the liquid again over the course of several hours might also prove to be an effective use of the mechanism, it is expected that this apparatus will allow sufficient light to the bottom of each baffle such that the microorganisms will be able to thrive over the entire surface of these "transparent rocks" because they not only provide a surface on which to grow, but also the photosynthetic requirements of the chloroplasts. It is quite possible that increasing the exterior surface area of the baffles by providing grooves or ridges on the surface might also enhance cultivation yields, however such a system is likely to require additional handling to remove the microorganisms from such roughened surfaces. In this case it might be desirable to remove all the baffles from a tank with a single lift hoist at one time, and provide a complete set of baffles from the previous tank that have been processed to remove the algae. Such a practice might seem to add to the danger of cross-contamination between tanks (any particular set of baffles would move progressively to the next tank with each harvesting operation), but this can be avoided by simply never moving the baffle sets more than to the next adjacent tank by processing in one direction in a given harvest and the opposite direction in the next harvest. The result of this alternating directions each time is that any given set of baffles would never be in any more than a total of three tanks, giving some degree of isolation from a single contamination spreading to every tank. Furthermore, since each tank is independent, unlike large shallow ponds or continuous raceway configurations, the compartmentalization in itself is a measure of protection against complete collapse of any given crop, although breeder batches should always be maintained, and the age of a colony should not be allowed to exceed the maximum average lifespan for whatever particular species is under cultivation.

The sparging piping at the bottom of the tank should be sufficient to allow for both addition of carbon dioxide and other nutrients as would be facilitated by a manifold of various supply lines (not shown) ahead of the pump. Operators might want to consider using a pump with far more capacity than would be required to feed the colonies, since it is quite possible that the same sparging lines could be used as a method of flotation de-watering at any time that the entire colony in the tank is to be harvested (e.g., prior to re-inoculation with new parent cells or a change of species).

With reference now to FIGS. 5-8, in one aspect of the invention, one embodiment of a grow box is illustrated generally at 100. The grow box is essentially a light delivery apparatus for introduction and distribution of light into a growth medium to facilitate the efficient growth of phytoplankton and other autotrophic aquatic species. The grow box comprises a plurality of elongated baffles 102. Each baffle 102 has two generally parallel side walls 104 and a bottom wall 106 interconnecting the side walls 104. The side walls and bottom wall define deep, elongated, trough-like enclosures 108. The upper edge portions 110 of adjacent pairs of baffles 102 are joined by horizontally disposed bridge walls 112. In this manner, each of the baffles is freely suspended from the one or two bridge walls that join the upper edge portions of each baffle with directly adjoining baffles such that each baffle is spaced apart from each adjacent baffle by the width of the interconnecting bridge walls, thereby forming a plurality of spaced-apart baffles. The plurality of baffles is capped by a top chamber 114, comprising a top panel 116 and a pair of opposing side panels 118 depending from the edges of top panel 116 and extending generally parallel to the plurality of baffles 102. Each side panel 118 is integrally connected to one of the side walls 104 of one of the baffles 102. Two end panels 120 are affixed to and seal the opposite longitudinal ends of the baffles 102 and top chamber 114 to form a completely integrated enclosure having a hollow interior and generally characterized on the top by the top chamber 114 and baffles 102 extending downwardly from the top chamber. The upper edge portions 110 of the sides walls 104 of each of the plurality of baffles 102 are spaced apart to define a plurality of elongated openings 109 such that the top chamber and baffles are in open communication via openings 109. Sealable aperture 122 is provided in the top panel 116 for introduction of water or other liquid into the apparatus. One or more check valves 124 are provided to equalize pressures inside the apparatus with respect to ambient pressures, as may be caused by heating and cooling cycles. Adjacent pairs of baffles are sufficiently spaced apart such that light distributed by the baffles 102 between the pairs of baffles encourages cultivation of phytoplankton or other autotrophic species in the liquid medium immediately surrounding and adjacent to the baffles 102. The depth of each baffle can generally be determined by the depth at which light will penetrate from top to bottom a wall of water disposed in the baffle enclosures. At some point, insufficient light will penetrate to the bottom of each baffle through water to encourage surrounding phytoplankton to cultivate. Applicants have therefore determined that a reasonable depth for each baffle is between 6 and 24 inches, with an optimal depth of approximately 12 inches. While the illustrated embodiments show the apparatus having a plurality of baffles, it will be understood by those of skill in the art that the apparatus could be made with only one baffle depending from a top chamber.

In operation, each apparatus is introduced into a liquid medium containing a selected species of phytoplankton. Water 126 is introduced into each of the baffle enclosures, up to approximately the level of bridge walls 114, thus effectively sinking the apparatus to the level of the bridge walls. The top chamber remains filled with air, and therefore provides a buoy-like effect, which stabilizes the apparatus, and helps to maintain it at a height such that the entire vertical extent of the baffles are introduced into the growth medium. At least a majority of the surfaces of the apparatus must be made of transparent materials to permit transmission of light through the top panel and top chamber, into the water in the baffles and through the side and bottom walls 104, 106 and end panels 120 of the baffles into the surrounding medium. The apparatus thus dramatically increases the growth area available for biomass production as compared to the horizontal footprint of the device. It is anticipated that natural light will be used as a light source, although artificial sources of light are contemplated to be within the scope of the invention.

Figure 13:
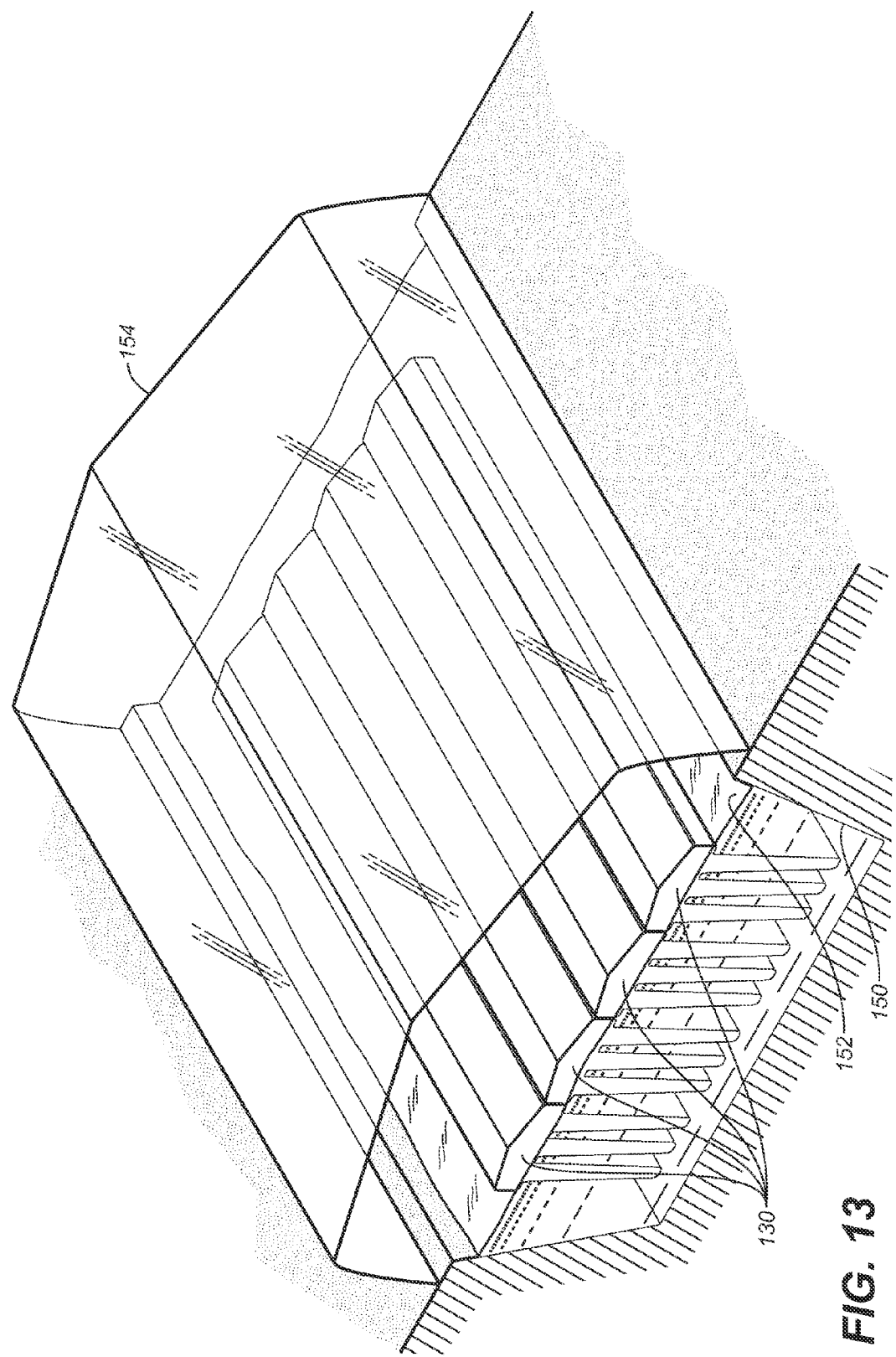
FIG. 13 is an upper perspective view of a plurality of light distribution apparatuses of the type shown in FIGS. 9-12 grouped in an array in which they would typically be deployed in normal use in a liquid medium.

Finally, FIG. 13 illustrates a plurality of growth box devices 130 grouped in an array in which they would typically be inserted into a liquid impermeable tub or basin 150 containing liquid growth medium 152. A lid 154 over the basin prevents the growth medium from being contaminated by substances inconsistent with the apparatus's use as a bioreactor. It is contemplated that periodically the tub will be partially drained to harvest biomass grown in the medium, whereupon the tub can be refilled, and nutrients introduced through inlets and ports of the type well known to those of skill in the art.

There have thus been described certain preferred embodiments of an apparatus for cultivation of phytoplankton and other autotrophic aquatic species. While preferred embodiments have been described and disclosed, it will be recognized by those with skill in the art that modifications are within the true spirit and scope of the invention. The appended claims are intended to cover all such modifications.

We claim:

1. A light distribution apparatus for cultivation of phytoplankton and other autotrophic aquatic species in an aquatic medium, the apparatus comprising:

a plurality of elongated baffles, each baffle having two generally parallel side walls and a bottom wall interconnecting said side walls, said side and bottom walls bounding a deep, trough-like enclosure, each side wall having an upper edge portion, the upper edge portions of the sides walls of each of said plurality of baffles spaced apart defining a plurality of elongated openings, a plurality of horizontally disposed bridge walls extending longitudinally along and joining the upper edge portions of the side walls of adjacent pairs of said baffles, each of said plurality of baffles freely suspended from at least one of said bridge walls such that each baffle is spaced apart from each adjacent baffle, a top chamber defined by a generally horizontal top panel, a pair of opposing side panels, and said plurality of bridge walls, said top panel vertically spaced from said plurality of bridge walls, each of said pair of side panels depending from said top panel, extending parallel to said baffles and affixed to the upper edge portion of one of the side walls of one of said baffles, said top chamber in communication with the enclosure of each of said plurality of baffles through said plurality of openings, each of said plurality of baffles and said top chamber having opposite ends, and a pair of transversely extending end walls affixed to and sealing the ends of said plurality of baffles and said top chamber thereby forming a completely integrated enclosure having a hollow interior.

2. The light distribution apparatus of claim 1 wherein:
means for introduction of liquids into said enclosure.

3. The light distribution apparatus of claim 1 wherein:
means for controlled admission into and release from said top chamber of gases.

4. The light distribution apparatus of claim 1 wherein:
said top panel and said side walls of said baffles are transparent.

5. The light distribution apparatus of claim 4 wherein:
said baffles have a bottom portion, and
when said enclosures are filled with water and when said top panel is exposed to a light source, sufficient light penetrates through said water and through said baffles to permit cultivation of phytoplankton in a surrounding liquid medium adjacent said baffles.

6. The light distribution apparatus of claim 1 wherein:
side, bottom and end walls are liquid impervious.

7. The light distribution apparatus of claim 1 wherein:
the distance between said side each of said baffles defines a thickness, and
said adjacent pairs of baffles are spaced apart a distance approximately equivalent to said thickness.

8. The light distribution apparatus of claim 1 wherein:
said baffles are spaced apart between approximately one inch and approximately six inches.

* * * * *